United States Patent
Sowinski et al.

(10) Patent No.: US 7,879,085 B2
(45) Date of Patent: Feb. 1, 2011

(54) EPTFE CRIMPED GRAFT

(75) Inventors: Krzysztof Sowinski, Wallington, NJ (US); Jamie S Henderson, Oakland, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/236,261

(22) Filed: Sep. 6, 2002

(65) Prior Publication Data
US 2004/0049264 A1 Mar. 11, 2004

(51) Int. Cl.
*A61F 2/06* (2006.01)

(52) U.S. Cl. .............. 623/1.28; 623/1.32; 623/1.46

(58) Field of Classification Search .......... 623/1.28, 623/1.32, 1.46
See application file for complete search history.

(56) References Cited

U.S. PATENT DOCUMENTS

| | | | |
|---|---|---|---|
| 3,029,819 A | 4/1962 | Edward | |
| 3,337,673 A * | 8/1967 | Jeckel | 264/324 |
| 3,730,229 A | 5/1973 | D'Onofrio | |
| 3,878,565 A * | 4/1975 | Sauvage | 623/1.5 |
| 4,164,045 A * | 8/1979 | Bokros et al. | 623/1.28 |
| 4,743,480 A | 5/1988 | Campbell et al. | |
| 4,876,051 A | 10/1989 | Campbell et al. | |
| 4,892,539 A * | 1/1990 | Koch | 623/1.52 |
| 4,955,899 A | 9/1990 | Della Corna et al. | |
| 5,282,847 A * | 2/1994 | Trescony et al. | 623/1.29 |
| 5,556,426 A | 9/1996 | Popadiuk et al. | |
| 5,607,478 A | 3/1997 | Lentz et al. | |
| 5,609,624 A | 3/1997 | Kalis | |
| 5,628,786 A | 5/1997 | Banas et al. | |
| 5,695,517 A * | 12/1997 | Marin et al. | 623/1.13 |
| 5,697,970 A | 12/1997 | Schmitt et al. | |
| 5,993,483 A | 11/1999 | Gianotti | |
| 6,027,779 A | 2/2000 | Campbell et al. | |
| 6,053,938 A | 4/2000 | Goldman et al. | |
| 6,080,198 A * | 6/2000 | Lentz et al. | 128/898 |
| 6,352,554 B2 * | 3/2002 | De Paulis | 623/1.26 |
| 6,416,537 B1 | 7/2002 | Martakos et al. | |
| 6,719,784 B2 | 4/2004 | Henderson | |
| 7,056,412 B2 | 6/2006 | Henderson | |
| 2002/0058993 A1 * | 5/2002 | Landau et al. | 623/1.35 |
| 2002/0123790 A1 * | 9/2002 | White et al. | 623/1.14 |
| 2003/0017775 A1 * | 1/2003 | Sowinski et al. | 442/315 |
| 2003/0149471 A1 * | 8/2003 | Briana et al. | 623/1.13 |
| 2004/0098077 A1 | 5/2004 | Gianotti | |

(Continued)

FOREIGN PATENT DOCUMENTS

DE 4430485 C1 * 3/1996

(Continued)

*Primary Examiner*—Paul Prebilic
(74) *Attorney, Agent, or Firm*—Vidas, Arrett & Steinkraus P.A.

(57) ABSTRACT

The present invention provides an expanded tubular graft formed of expanded polytetrafluoroethylene (ePTFE). The graft has first and second open ends and a surface longitudinally extending between the ends. The graft also includes an inner and outer cylindrical walls, where the walls have crimps or corrugations located along the surface of the graft. Additionally, the graft is coated with biocompatible elastomer covering portions of the outer cylindrical walls of the PTFE graft. The resulting ePTFE crimped graft exhibits various enhanced properties, such as adjustable graft length, high kink resistance, improved suture retention and high crush resistance as compared to the same graft without the crimps.

15 Claims, 6 Drawing Sheets

U.S. PATENT DOCUMENTS

2006/0293744 A1  12/2006  Peckham et al.
2008/0228262 A1*  9/2008  Goldmann et al. ......... 623/1.28

FOREIGN PATENT DOCUMENTS

| EP | 1054648 | 6/2004 |
|---|---|---|
| FR | 2334488 | 7/1977 |
| JP | 6-64495 | 3/1994 |
| JP | 09-241412 | 9/1997 |
| JP | 2000-279530 | 10/2000 |
| JP | 2001-224609 | 8/2001 |
| WO | WO 83/03349 | 10/1983 |
| WO | WO 87/05796 | 10/1987 |
| WO | 9826731 | 6/1998 |
| WO | 00/43052 | 7/2000 |
| WO | WO 02/100454 | 12/2002 |

* cited by examiner

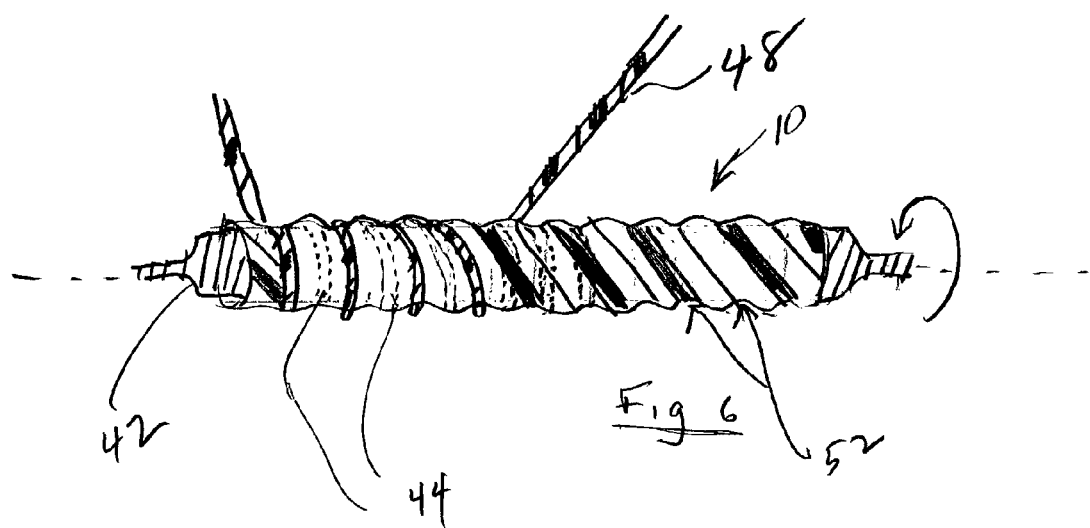
Fig 6
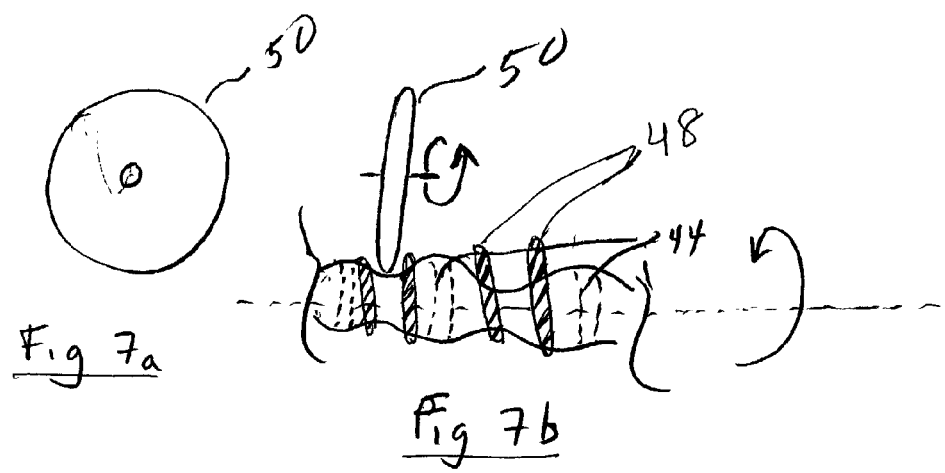
Fig 7a
Fig 7b

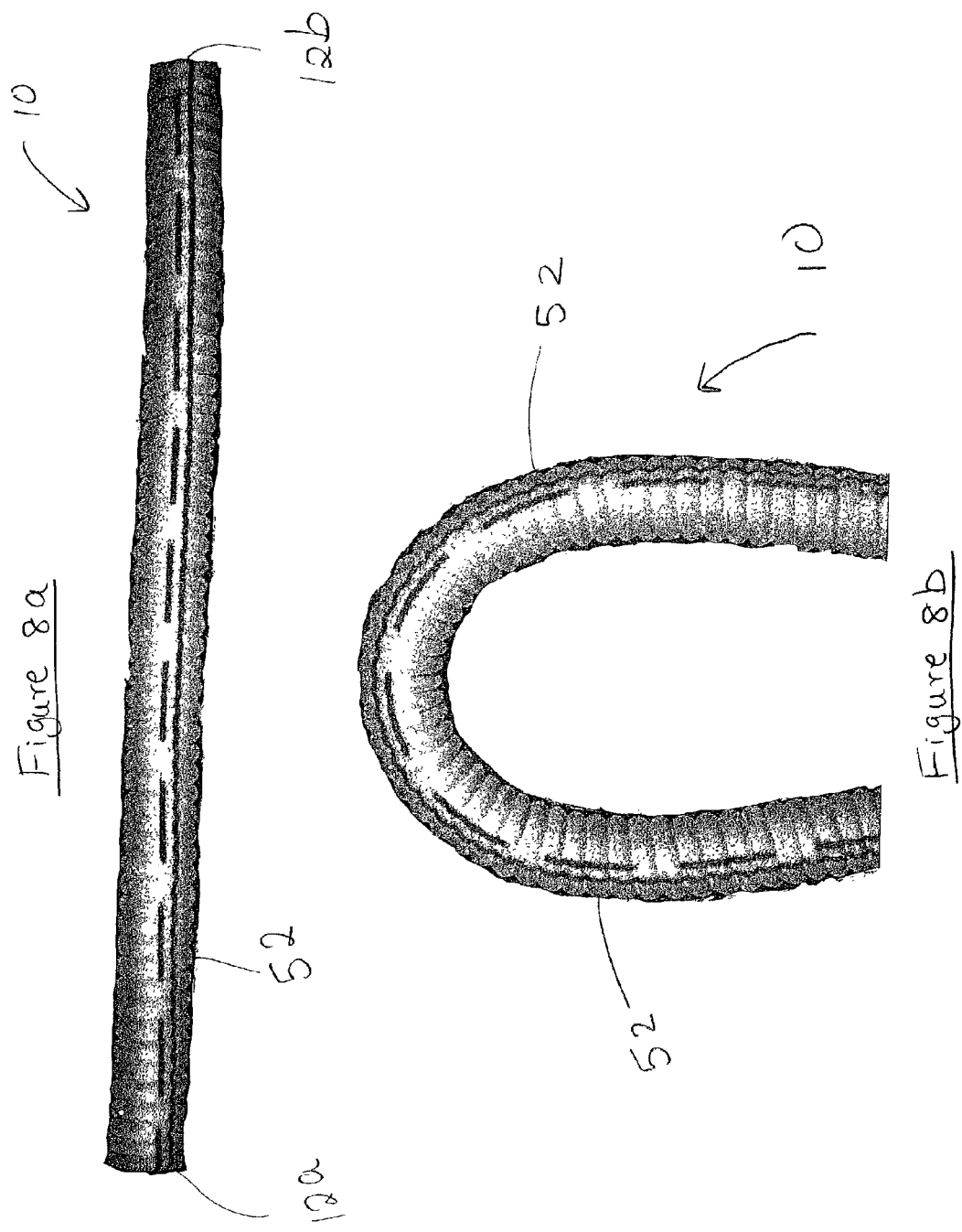

EPTFE CRIMPED GRAFT

FIELD OF THE INVENTION

The present invention relates generally to PTFE vascular prostheses. More particularly, the present invention provides a crimped graft formed of expanded polytetrafluoroethylene (ePTFE) which exhibits adjustable graft length, high kink resistance, improved suture retention and high crush resistance.

BACKGROUND OF RELATED TECHNOLOGY

It is well known to utilize PTFE and ePTFE to form vascular prostheses. It has also been known to utilize yarn or filament in wraps in combination with ePTFE grafts. For example, U.S. Pat. No. 5,607,478 to Lentz et al. shows wrapping a graft of ePTFE tubular structure with a PTFE yarn in a helical fashion to form an ePTFE graft with increased suture retention strength, radial tensile strength, crush resistance and tear propagation resistance. U.S. Pat. No. 5,556,426 to Popadiuk et al. discloses a luminal device made from a porous cylindrical PTFE tube. A fluoropolymer such as PTFE filament or coil is wrapped helically around the external surface of the tube to form a radially reinforced flexible PTFE implantable prosthesis. U.S. Pat. No. 4,955,899 to Della Corna et al. teaches compressing a portion of a porous PTFE tube along its longitudinal axis and coating of biocompatible elastomer is applied to the outer wall of the compressed portion of the PTFE tube to provide a longitudinally compliant PTFE graft which minimizes suture hole bleeding, increases suture strength and reduces serious seepage. As discussed above, although the prior art patents show ePTFE grafts with several enhanced properties, none of them show crimping an ePTFE graft.

It is, therefore, desirable to provide crimps in a vascular graft formed of a tubular ePTFE tube, which provides length adjustability as well as improves resistance to kinking, suturing properties, and other handling characteristic such as crush resistance.

SUMMARY OF THE INVENTION

The present invention provides an expanded tubular graft formed of expanded polytetrafluoroethylene (ePTFE). The graft includes inner and outer cylindrical walls and first and second ends. The wall defines a surface longitudinally extending between the ends. The walls having crimps partially or fully along their length to provide adjustability of the ePTFE vascular graft length as compared to the same graft without the crimps. Additionally, the graft may be coated with a biocompatible elastomer covering a selection portion or all of the graft wall, and optimally penetrating its node and fibril structure.

The term "crimped" as used in the present invention indicates a circumferential corrugation which is a wave-like silhouette to the graft and permits enhanced properties. In particular, this term includes an arcuate crimp shape as shown in the figures below.

The crimped ePTFE grafts of the present invention may optionally be employed in combination with a stent to form a stent/graft device, and may be used with bioagents useful in preventing inflammation, immunoresponse by the body, infection, coagulation and the like.

BRIEF DESCRIPTION OF DRAWINGS

FIG. 6 further shows an assembly for making a crimped ePTFE vascular graft of the present invention.

FIG. 7 shows a fixture which may be employed as part of the assembly for making the ePTFE crimped grafts of the present invention.

FIGS. 8a, 8b, and 8c are illustrations of a crimped ePTFE graft of the present invention.

DETAILED DESCRIPTION OF THE INVENTION

The prostheses of the present invention are tubular structures which are particularly suited for use as luminal grafts. The crimped grafts of the present invention may be used in a variety of applications requiring repair or replacement of a body lumen. The crimped grafts of the present invention have particular use as vascular grafts, both for surgical and endoluminal (minimally invasive) applications. The prosthesis is formed of extruded polytetrafluoroethylene (PTFE), as PTFE exhibits superior biocompatibility. Further, PTFE is particularly suitable for vascular applications as it exhibits low thrombogenicity. Tubes formed of extruded PTFE may be expanded to form ePTFE tubes where the ePTFE tubes have a desired fibrous state which is defined by elongated fibrils interconnecting spaced apart nodes. Such node/fibril arrangement defines a microporous structure, the porosity of which is determined by the distances between the nodes generally referred to as the internodal distance (IND). In forming tubular vascular grafts, the porosity of the tubular structure is selected so as to have desirable healing and ingrowth characteristics. A balance must be achieved between a porosity sufficient to permit endothelialization and tissue ingrowth, while concurrently providing a structure which exhibits sufficient physical integrity to successfully function as a vascular graft. The present invention provides a crimped PTFE tubular structure which, among its many advantages, exhibits length adjustability, high kink resistance, superior suture retention strength and high crush resistance.

Figure 1:
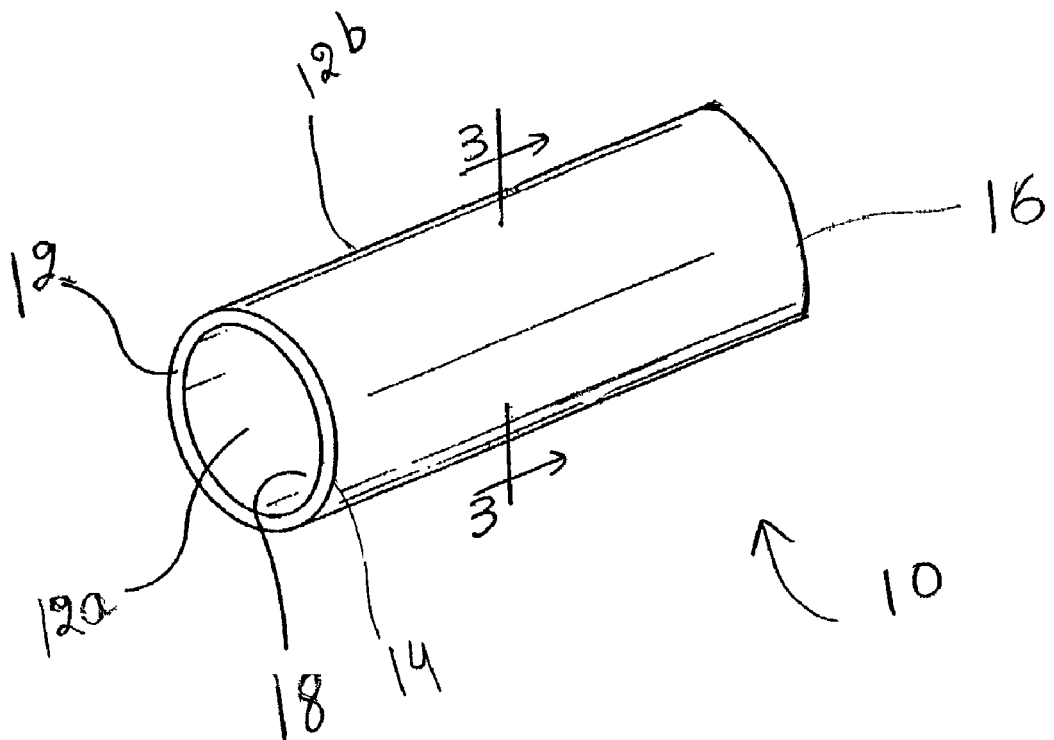
FIG. 1 is a perspective showing a portion of an ePTFE tube used in accordance with the present invention.
Figure 2:
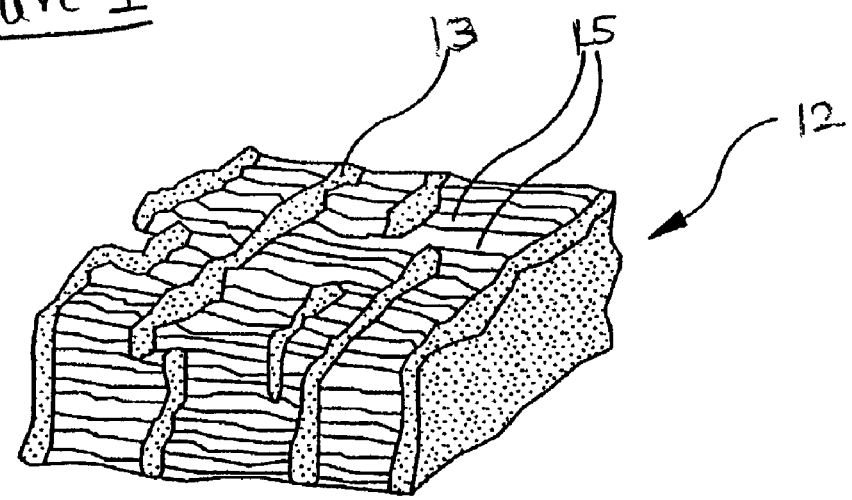
FIG. 2 is a schematic representation of the microstructure of the wall of the ePTFE tube of FIG. 1.

Referring now to FIGS. 1 and 2, there is illustrated a first embodiment of the present invention. Tubular graft 10 is an elongate generally tubular body including a generally thin hollow generally cylindrical wall 12 with a first open end 14 and a second open end 16. The wall 12 also includes inner and outer surfaces 12a and 12b, respectively. The tubular graft 10 defines an inner lumen 18 extending longitudinally therethrough. The inner lumen 18 allows a passage of fluid, e.g., blood through the graft subsequent to deployment in the body. Graft 10 can be tailored to have any desired length and internal diameter to fit the intended application. Various shapes and configurations may also be employed. For example, bifurcations, extensions off a main tubular trunk section, tapers, and stepped and flared grafts are among the many shapes and configurations useful in the present invention. Graft 10 is formed of PTFE in a paste extrusion process. The process for the paste extrusion of PTFE tubes is well known in the extrusion art, as will be described in detail below. Subsequent to formation of an extruded PTFE tube 10, expansion of the tube to form ePTFE having nodes 13 and fibrils 15 in an arrangement which defines the microporous structure is generally accomplished using known techniques. The use of ePTFE is generally favored for most implant applications because it provides a means for neointimal growth and encapsulation which in most vascular applications is desirable and encourages patency.

As exemplified by Popadiuk et al., U.S. Pat. No. 5,556,426 issued Sep. 17, 1996, which is hereby incorporated by reference, a dispersion of a fluoropolymer powder or coagulated dispersion, preferably highly crystalline PTFE, is initially mixed with a liquid lubricant and shaped. The lubricant is desirably capable of wetting the fluoropolymer surface, and of being removed by evaporation or extraction at a temperature below the crystalline melting point of the fluoropolymer.

Examples of suitable lubricants include liquid hydrocarbons such as solvent naphtha, white oil, etc.; aromatic hydrocarbons such as toluene, xylene, etc.; alcohols; ketones; esters; silicone oils; fluorocarbon oils; aqueous systems containing surfactants; and mixtures thereof. A particularly preferred lubricant is a synthetic isoparaffinic hydrocarbon available as ISOPAR® from Exxon Chemical Americas, Houston, Tex. ISOPAR® has a boiling point of about 154°-176° C.

The amount of lubricant to be used will vary according to the conditions of extrusion, the size of the desired product, and the nature and amount of the fluoropolymers and any additives included in the feedstock. The lubricant may be included in the feedstock in an amount of from about 10 wt. % to about 30 wt. %. Preferably, the lubricant is included in the feedstock in an amount of from about 15 wt. % to about 20 wt. %.

The lubricant is then removed from the extrudate. The resulting dried extrudate then will be stretched or "expanded" at a desired rate, usually at an elevated temperature, which is nonetheless below the crystalline melting point of the tetrafluoroethylene polymer resin. While being held in the stretched state, the tetrafluoroethylene extrudate may be sintered by heating the stretched extrudate to a temperature above the crystalline melting point of the fluoropolymer sintering "locks in" the microporous structure. This process produces a material having a microstructure composed of nodes interconnected by variably sized fibers, also known as fibrils or microfibrils. This microstructure greatly increases the tensile strength of the tetrafluoroethylene polymer extrudate.

Expansion is a term well known in the art and may be performed according to the methods known in the art. Generally, tubes may be expanded using preselected processing parameters such as rates of expansion and temperatures at various processing states which develop a desired microporous structure. The specifically selected microporous structure of the resulting graft tube has predetermined porosity suitable to enhanced tissue in growth and cell endothelialization, thus providing good healing characteristics.

Generally, expansion involves stretching the extrudate in either the axial or the radial dimension, and often involves simultaneous stretching in both the axial and radial directions. The expanding may be performed at temperatures ranging from about ambient temperature to an elevated temperature that is below the crystalline melting point of the fluoropolymer. The preferred temperature at which the expanding process may be performed is from about 100° C. to about 300° C., taking advantage of the fluoropolymer's thermoplastic properties. Desirably, the expanding is performed at a temperature of the extrudate of between about 150° C. and about 280° C. Most desirably, the temperature of the extrudate during the expanding step is between about 260° C. and about 270° C. The stretching ratio is commonly between about 20% and about 4000%. Desirably, the stretching ratio is between about 200% and about 1500%. The resulting radially expanded graft tube 30 is suitable for use as an implantable vascular graft.

Figure 3:
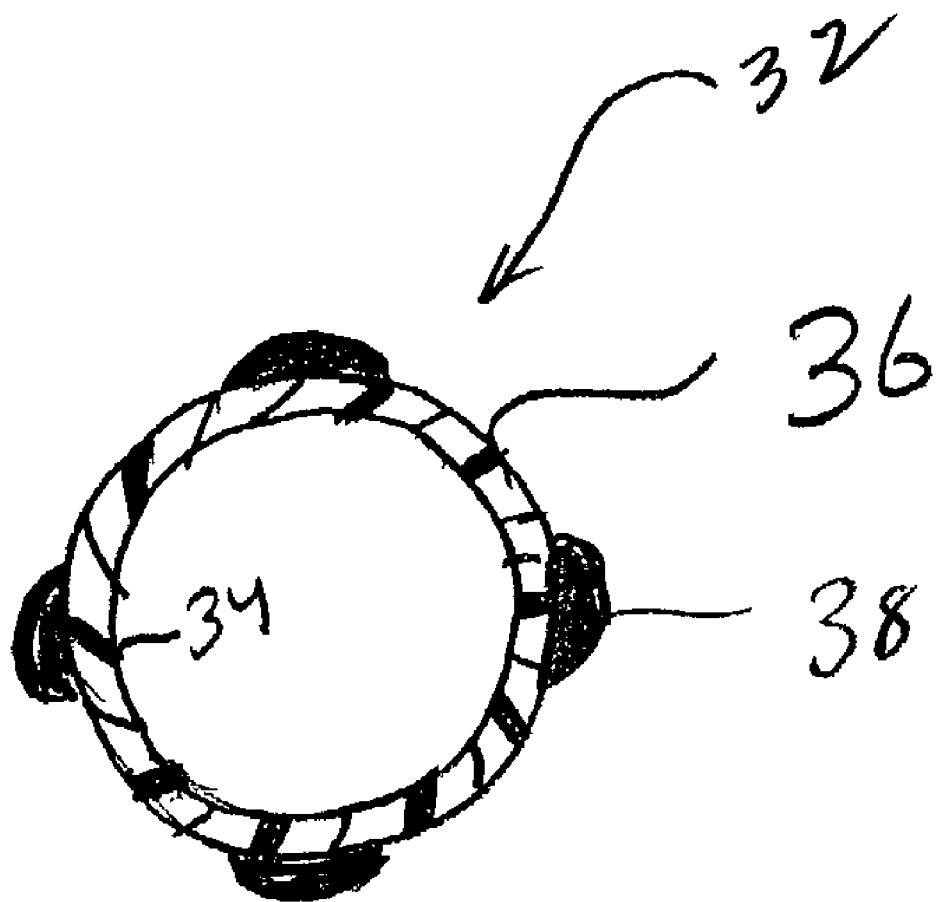
FIG. 3 is a cross-sectional drawing of the graft shown in FIG. 1 taken through the lines designated 3-3 within FIG. 1.

In FIG. 3, a cross section drawing of ePTFE graft 10 is shown, taken through the lines designated 3-3 within FIG. 1. Graft 10 includes an expanded porous PTFE tube 32 having a microstructure characterized by nodes interconnected by fibrils. ePTFE tube 32 includes an inner cylindrical wall 34 and opposing outer cylindrical wall 36. As shown in FIG. 3, outer cylindrical wall 36 optionally has a partial coating or layer around its circumference of a biocompatible elastomer 38, which provides enhanced stretchability and elastomeric recovery. Preferably, the coating could also penetrate deep into the spaces between the nodes and fibrils of the microstructure of the ePTFE tube 32. In one desirable embodiment of the invention, outer wall 36 is coated with elastomer 38 at selected locations around its circumference, desirably at 90-degree angles as shown in FIG. 3. Elastomer coating in this manner makes an adjustable ePTFE vascular graft length so that subsequent to being fully formed, e.g., after expansion and sintering, the graft may be stretched radially, without occurrence of plastic deformation of the node and fibril structure and when radial expansive force is removed, it easily and readily comes back to its approximate original position. Additionally, elastomer coating at selected portions of the graft minimizes suture hole tear at those points of the graft where the graft is anastomosed to blood vessels within the body, thereby increasing suture retention strength. Moreover, puncturing of the graft at the elastomeric coating portions of the graft, such as by a needle, demonstrates a self-sealing feature due to the elastomer.

In regard to the elastomeric coating 38 shown in FIG. 3, such elastomeric coating is selected to be a biocompatible elastomer and may be selected from a variety of materials, including, without limitation, fluorinated ethylene propylene (FEP), silicone rubber elastomers including medical-grade silicone rubber elastomers, segmented polyurethanes, polyurethane-ureas, polyurethane-polycarbonate copolymers, silicone-polyurethane copolymers and combinations thereof. Suitable candidates for use as elastomeric coating 38 typically have a Shore hardness rating between 50A-100A or 55D-60D. Most of the above-mentioned elastomers can be chemically or biologically modified to improve biocompatibility. Such modified compounds are also candidates for use in forming elastomeric coating 38 shown in FIG. 2.

Apart from biocompatibility, other requirements of an elastomer to be a suitable candidate for use as elastomeric coating 38 are that the elastomer be sufficiently elastic to maintain compressed portions of PTFE tube 32 in the compressed condition when vascular graft 10 is not being stretched. The elastomer should also be sufficiently elastic to effect rapid closure of suture holes formed by a suture needle. Elasticity should be balanced against the thickness of elastomeric coating 38, the objective being to select the minimum coating thickness necessary to prevent significant blood leakage through the suture hole locations without significantly impeding suture needle penetration and without adding unnecessary thickness to the graft. Yet another requirement of such elastomers is that they be easily dissolvable in low boiling point organic solvents such as tetrahydrofuran, methylene chloride, trichloromethane, dioxane, and dimethylformamide, by way of example. Finally, suitable elastomers desirably lend themselves to application to PTFE tube 32 by either the dip coating or spray coating methods well known in the art. Other coating methods, including using pressure to impregnate the node and fibril structure as well as coat the inner or outer wall of the graft, or disperse into elastomer itself may be employed for the drug delivery.

Moreover, portions of the ePTFE tube of the graft of the present invention may be coated or otherwise incorporated therein with one or more agents, such as bio-therapeutic agents. These bio-therapeutic agents include pharmaceutical agents. Such a material may be used to target therapeutic agents to specific sites of the body. Any drug or bio-therapeutic agent may be coated or incorporated therein. Examples of suitable drugs or bio-therapeutic agents may include, without limitation, thrombo-resistant agents, antibiotic agents, anti-tumor agents, cell cycle regulating agents, their homologs, derivative, fragments, pharmaceutical salts, and combinations thereof.

Useful thrombo-resistant agents may include, for example, heparin, heparin sulfate, hirudin, chondroitin sulfate, dermatan sulfate, keratin sulfate, lytic agents, including urokinase and streptokinase, their homologs, analogs, fragments, derivatives and pharmaceutical salts thereof.

Useful antibiotics may include, for example, penicillins, cephalosporins, vancomycins, aminoglycosides, quinolones, polymyxins, erythromycins, tetracyclines, chloramphenicols, clindamycins, lincomycins, sulfonamides, their homologs, analogs, fragments, derivatives, pharmaceutical salts and mixtures thereof.

Useful anit-tumor agents may include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

Useful anti-viral agents may include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof.

In order to achieve enhanced properties, especially properties relating to adjustable ePTFE vascular graft length, with high kink resistance, high suture retention and high crush resistance, the graft 10 is crimped as described below.

Figure 4A:
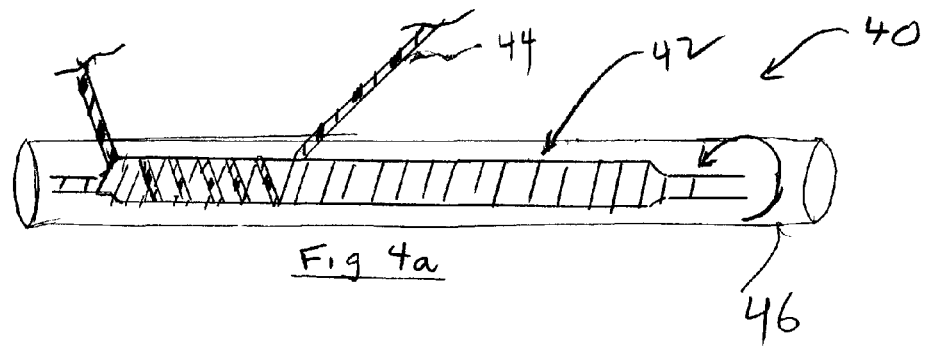
FIGS. 4a, 4b and 5 show portions of an assembly for making crimped ePTFE vascular graft in accordance with the present invention.
Figure 4B:
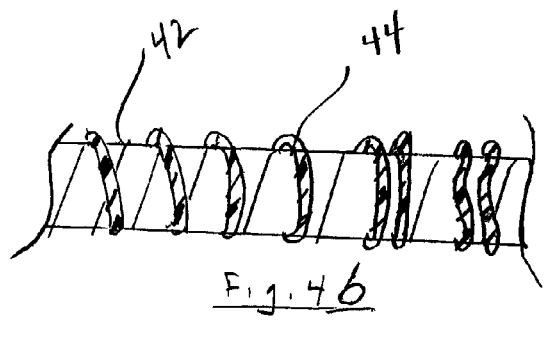

FIG. 4 illustrates one method for making crimped ePTFE vascular grafts of the present invention. With particular reference to FIG. 4a, there is shown an assembly 40 for crimping the ePTFE vascular graft 10 of the present invention. Assembly 40 consists of an inner mandrel 42 and an expansion mandrel 46. Both inner and expansion mandrels 42 and 46 are desirably made of stainless steel or other suitable material. The inner mandrel 42 is wrapped with coil bead 44 to form a pattern on the mandrel. The coil bead 44 is desirably made from fluorinated ethylene propylene (FEP) or wire or any other suitable material or polymer that holds the shape at certain temperatures. The coil bead will provide a raised surface over which graft 10 will be concentrically placed. The size and shape of the coil bead can be chosen based on the size and shape of the depressed crimp pattern sought to be made in the graft surface. For example, the coil bead 44 may be generally circular or oval in cross-sectional diameter, as shown in FIG. 4a, or it may take a different shape, such as a wedge or semi-circular cross-sectional shape. Accordingly, the thickness or diameter of the coil bead will vary depending on the depth of the impression to be made, i.e., the depth of the crimp trough. Generally, coil bead 44 has a diameter of about 0.005 inches to about 0.5 inches and desirably about 0.020 inches to about 0.040 inches. The coil bead may also be wound about the mandrel in any manner, e.g., tightly wound such that adjacent windings are close to each other, or more spaced apart such that adjacent windings are more distant from each other. As shown in FIG. 4b, the coil bead windings 44 may also be slightly corrugated or wave-like in shape, also drawn in FIG. 4b. FIG. 4b is an enlarged section of the inner mandrel 42 of FIG. 4a. Thus, the coil bead 44 may be varied in its size, three-dimensional shape and length, as well as its shape as applied to the mandrel, all such variations serving to provide a template from which to form the crimped grafts of the present invention. Mandrel 46 is selected to have an outer diameter (OD) which has a close fit tolerance with an inner diameter (ID) of inner mandrel 42, but which allows inner mandrel 42 to be placed inside mandrel 46 and readily removed therefrom.

Figure 5:
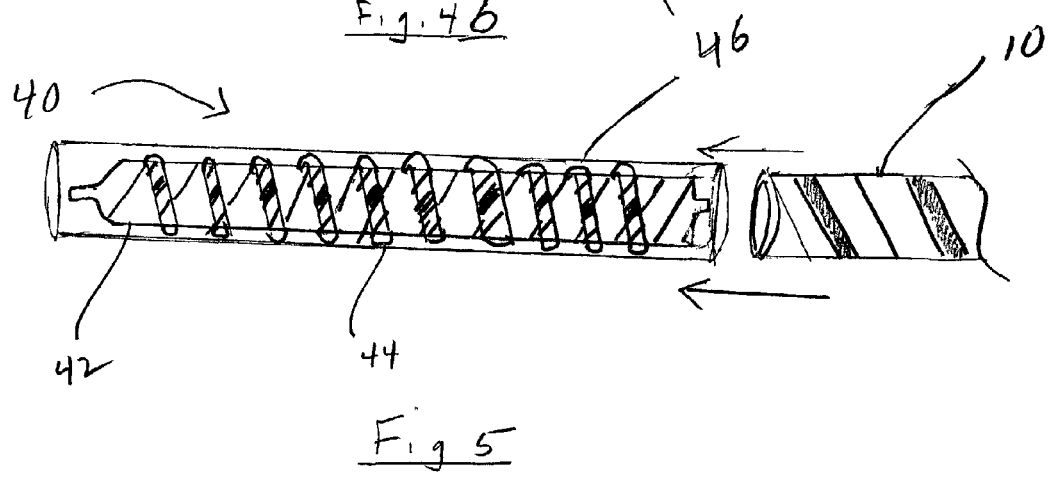

Referring again to FIG. 5, there is shown an ePTFE graft tube 10, e.g., an 8 mm long graft with an inside diameter of about 7.60 mm and wall size of preferably approximate 0.550 mm. Tubular graft 10 is placed over mandrel 46 and the graft is expanded slightly due to the closely matching dimensions of the mandrel OD and the graft ID.

FIG. 6 shows graft 10 being placed over inner mandrel 42 and coil bead 44. Desirably, the graft is snugly fitted about the underlying template such that a slight radial stretching of the graft may preferably be required prior to pulling the graft over the mandrel and coil bead assembly. In one embodiment of the invention, a second coil bead 48 is wrapped about graft 10 once it is disposed about assembly 40. The second coil is circumferentially disposed and wrapped such that it fits within the spaces or troughs formed by coil bead 44. The juxtapositioning of the two coil beads, coupled with appropriate tension (force), form the desired crimped impression in the ePTFE surface of graft 10.

Alternatively, a crimp template can be formed on a mandrel by etching or engraving the mandrel to the desired crimp size and shape. The ePTFE graft to be crimped can then be placed over the template and pressure applied, desirably with heat, such that the graft receives and holds the impression of the underlying template. The use of an external mold fixture, wrap, negative or positive fluid pressure or shrink wrap material may be employed. Desirably, such pressure is accompanied by sufficient heat to set the crimped impression into the graft.

In a further embodiment, wheel 50, as shown in a perspective side view in FIG. 7a, can be used as an alternative to a second coil bead 48 on the external side of graft 10 to form crimps as shown in FIG. 7b. Wheel 50, or other similar fixtures, can be used to apply pressure to the graft surface and create crimps 52.

Once graft 10 is secure, a mechanical and/or thermal energy, i.e., mechanical force, fluid pressure, heat, pressure, or a combination of these alternatives, is applied on the outer cylindrical wall to cause the imprint of the underlying pattern of the bead mandrel 42 to form crimps at the inner cylindrical wall between the first and second end of the graft. Similarly, such mechanical and/or thermal energy may also be applied to the inner cylindrical wall to form crimps within. The graft 10 is wrapped externally about the outer cylindrical wall, preferably by hand using another coil, such as a fluorinated ethylene propylene (FEP) coil bead wound about in the troughs formed by the underlying coil bead template. The coil is thus spirally wrapped to fit within spiral openings of the underlying coil bead template. The graft forms around the wires in alternating pattern, thus creating the desired shape of the crimp.

The graft 10 may preferably be heated to set the desired crimp pattern. For example, graft 10 may be desirably placed in an oven for a sufficient time and at a sufficient temperature to heat-set the crimps, for example, ten minutes, preferably a range of between and including about 420° F. to about 450° F. At temperatures higher than 450° F., the FEP coil bead may stick, which may be undesirable. After the oven cycle is completed the graft is demandreled and the outer and inner bead coils are removed. A second oven cycle may desirably be used to longitudinally compress to promote better crimp memory, for example, at about 5-12 minutes at 650-667° F. (343.3-352.7° C.). Finally, the graft is cooled to ambient temperature and prepared for use.

Figure 8C:
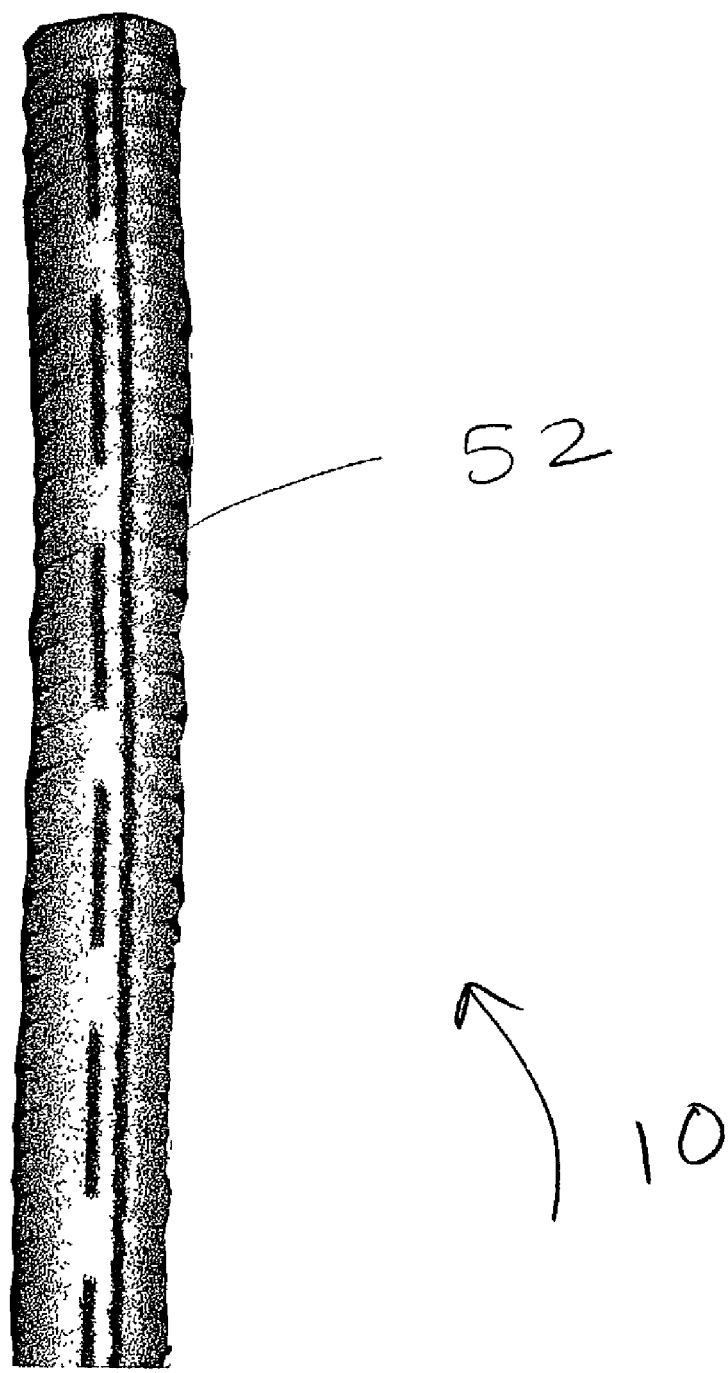

The resulting ePTFE crimped vascular graft 10 is shown in FIGS. 8a, 8b, and 8c. The crimped ePTFE graft 10 as illustrated in FIG. 8a shows the thin walled graft 12 having the first open end 12a and the second open end 12b. Graft 10 exhibits a fine alternating crimp pattern which includes a series of arcuate-shape crimps 52 therealong. The arcuate-shaped crimps 52 are extended uniformly from the first open end 12a to the second open end 12b over the entire graft 10. Moreover, as apparent from FIGS. 8a and 8b, the crimps with arcuate-shape patterns form a reversible structure over the entire graft 10. The inner and outer surfaces of the extruded wall of the graft comprise a single helical corrugation formed from a continuous spiral winding originating at one end of the graft and extending to the other end of the graft, wherein the single helical corrugation comprises a plurality of crimps.

Even though the graft shown in FIG. 8 reflects a fully crimped ePTFE graft 10, the ePTFE graft 10 may also preferably be partially crimped where the crimps are formed along one or more portions of the graft length. Also, even though the crimps formed as shown in the ePTFE graft 10 of FIG. 8 are uniform with arcuate-shape, the crimps of such ePTFE graft may preferably be non-uniform and vary in characteristics such as shape, length, height, diameter, etc.

Inventive crimped graft 10 has sufficient radial strength and flexibility to allow for deep bends, as shown in FIG. 8b, without kinking or radial collapse. Crimps 52 permit elongation on the outer wall side of the bead, and permit compression of the crimps on the closed side of the bend to prevent collapse of the tube and which resists pressure uniformly over the entire length of the tube. Thus, when the graft 10 is in a bending position shown in FIG. 8b, it does not kink or fold to the sections where the pressure is applied, thereby maintaining a uniform strength over the entire graft.

Furthermore, the inventive crimped graft 10 having longitudinally extending crimps is shown in FIG. 8c. The crimped graft 10 has sufficient longitudinal strength when expanded, exhibiting the graft 10 to be more flexible and having adjustable graft length.

Crimping in accordance with the method disclosed in the present invention results in arcuate-shaped crimps which provide strength over the surface of the graft, thus preventing the possibility of kinking or collapsing under pressure or during bending. Moreover, the elastomer coating on the graft in the manner described in the present invention exhibits enhanced suture retention strength, thereby minimizing the suture hole bleeding at the time of implantation, adjustable ePTFE vascular graft length due to the graft being crimped and expanded which is more flexible and capable of conforming to curves in the vascular system without undesirable kinking Although illustrative and preferred embodiments of the present invention have been described herein, it is to be understood that the invention is not limited to those precise embodiments, and that various changes and modifications may be effected therein by one skilled in the art, without departing from the spirit or scope of the invention.

What is claimed is:

1. An expanded tubular graft comprising:
   a tubular graft tube consisting of expanded polytetrafluoroethylene (ePTFE), said tubular graft having an extruded wall with inner and outer surfaces, and having first and second open ends;
   said extruded wall defining a surface longitudinally extending between said ends of the tubular graft;
   the inner surface of the extruded wall having only a single helical corrugation, the corrugation formed from a continuous spiral winding and the outer surface of the extruded wall having only a single helical corrugation, the corrugation formed from a continuous spiral winding, each of said corrugations having sections of variable diameter or variable shape.

2. The tubular graft of claim 1, wherein said corrugations provides high kink resistance as compared to the same graft without said corrugations.

3. The tubular graft of claim 1, wherein said corrugations provides high suture retention as compared to the same graft without said corrugations.

4. The tubular graft of claim 1, wherein said corrugations provides high crush resistance as compared to the same graft without said corrugations.

5. The tubular graft of claim 1, further comprising a coating of a biocompatible elastomer covering portions of said outer surface of the wall of said graft tube.

6. The tubular graft of claim 5, wherein the coating is formed at a 90 degree angle at the portions of said outer surface of the wall.

7. The tubular graft of claim 5, wherein said biocompatible elastomer is selected from a group of elastomers consisting of medical-grade silicone rubber elastomers, segmented polyurethanes, polyurethane-ureas, polyurethane-polycarbonate copolymers, silicone-polyurethane copolymers, and combinations thereof.

8. The tubular graft of claim 1, wherein said corrugations have a depth ranging from about 0.005 inches to about 0.5 inches.

9. The tubular graft of claim 1, wherein the corrugation sections are of variable diameter.

10. The tubular graft of claim 1, wherein the corrugation sections are of variable shape.

11. An expanded tubular graft comprising:
    a tubular graft formed of expanded polytetrafluoroethylene (ePTFE), said tubular graft having an extruded wall with inner and outer surfaces, and having first and second open ends;
    wherein said extruded wall defines a surface longitudinally extending between said ends of the tubular graft;
    the inner surface of the extruded wall having only a single impression, the impression having only a single helical wrapping which extends along the length of the graft, and the outer surface of the extruded wall having an impression, the outer surface impression having only a single helical wrapping which extends along the length of the graft; wherein said extruded wall is comprised of extruded ePTFE; and wherein said impressions comprise a plurality of sections of variable diameter or variable shape; said impressions providing length adjustability.

12. An expanded tubular graft comprising:

a tubular graft tube formed of expanded polytetrafluoroethylene (ePTFE), said tubular graft having an extruded wall with inner and outer surfaces, and having first and second open ends; and a coating of a biocompatible elastomer covering portions of said outer surface wall;

said extruded wall defines a surface longitudinally extending between said ends of the tubular graft;

the inner surface of the extruded wall having only a single helical corrugation formed from a continuous spiral winding and the outer surface of the extruded wall having only a single helical corrugation formed from a continuous spiral winding, each of the continuous spiral windings comprising a plurality of non-uniform sections of variable diameter, wherein said biocompatible elastomer is selected from a group of elastomers consisting of medical-grade silicone rubber elastomers, segmented polyurethanes, polyurethane-ureas, polyurethane-polycarbonate copolymers, silicone-polyurethane copolymers, and combinations thereof.

13. An expanded tubular graft comprising:

a tubular graft tube comprising expanded polytetrafluoroethylene (ePTFE), said tubular graft having an extruded wall with inner and outer surfaces, and having first and second open ends;

said extruded wall defining a surface longitudinally extending between said ends of the tubular graft;

the inner surface of the extruded wall having only one helical corrugation formed from a continuous spiral winding;

the outer surface of the extruded wall having only one helical corrugation formed from a continuous spiral winding;

each of the corrugations including sections of variable diameter, variable height, or variable shape.

14. The tubular graft of claim 13, wherein the sections are of variable diameter.

15. The tubular graft of claim 13, wherein the sections are of variable shape.

* * * * *